United States Patent [19]

Kyu

[11] Patent Number: 5,365,936
[45] Date of Patent: Nov. 22, 1994

[54] APPARATUS FOR DISPLAYING WAVEFORM OF PHYSIOLOGICAL SIGNAL

[75] Inventor: Kanki Kyu, Tokyo, Japan

[73] Assignee: Nihon Konden Corporation, Tokyo, Japan

[21] Appl. No.: 115,204

[22] Filed: Sep. 1, 1993

Related U.S. Application Data

[63] Continuation of Ser. No. 750,502, Aug. 27, 1991, abandoned.

[30] Foreign Application Priority Data

Aug. 31, 1990 [JP] Japan .................................. 2-90656

[51] Int. Cl.$^5$ ............................................ A61B 5/0402
[52] U.S. Cl. .................................. 128/710; 345/113
[58] Field of Search ........................... 128/710, 712; 324/121 R; 340/722, 734

[56] References Cited

U.S. PATENT DOCUMENTS 4,032,912  6/1977  Wood .
4,094,310  6/1978  McEachern et al. .
4,295,135  10/1981  Sukonick .

OTHER PUBLICATIONS

Datascope "Advanced Monitors for Anesthesia", Catalog, 1984.

"Datascope. The monitors of choice ... wherever you need them.", Catalog, 1984.

*Primary Examiner*—William E. Kamm
*Assistant Examiner*—Scott M. Getzow
*Attorney, Agent, or Firm*—Hoffmann & Baron

[57] ABSTRACT

An apparatus for displaying waveform of a physiological signal such as a cardiographic signal has a waveform display control device for picking up the physiological signal and for conducting a control for displaying the waveform of the physiological signal in the form of a continuous waveform or a freeze waveform, a pattern display control device for forming a pattern signal of a back scale which is displayed simultaneously with the waveform of the physiological signal and for conducting a control to vary the brightness of the display of the back scale depending on whether the waveform of the physiological signal is displayed in the form of the continuous waveform or the freeze waveform, and a display monitor device for displaying the physiological signal waveform and the back scale on a display screen thereof. When the apparatus is used in the mode for displaying the physiological signal in the form of a continuous waveform, the brightness of display of the back scale pattern signal is lowered or reduced to zero, whereas, when the apparatus is used in a mode for displaying the physiological signal in the form of a freeze waveform, the brightness of display of the back scale pattern signal is elevated.

8 Claims, 3 Drawing Sheets

APPARATUS FOR DISPLAYING WAVEFORM OF PHYSIOLOGICAL SIGNAL

This is a continuation of copending application Ser. No. 07/750,502 filed on Aug. 27, 1991, now abandoned.

BACKGROUND OF THE INVENTION

1. Field of the Invention

The present invention relates to an apparatus for displaying, for the purpose of observation, physiological signals such as a cardiogram on a monitor screen and, more particularly, to an apparatus for displaying physiological signal waveform together with a back scale to enable the waveform to be observed in a still state.

2. Description of the Related Art

Hitherto, in a so-called critical care unit (CCU) for example, means are provided for enabling continuous monitoring of physiological signals such as cardiographic signals thereby making it possible to effect a suitable treatment in the event of any abnormality occurring in the condition of the patient.

When physiological signals such as cardiographic signals are displayed on the monitor screen of a CRT (cathode ray tube) for the purpose of observation, the continuous waveform of such signals are displayed and, when any abnormal waveform is recognized, the waveform is made still and this still waveform, referred to as "freeze waveform", is output to a recorder which produces a hard copy of the waveform. The recorder prints the freeze waveform together with a back scale formed by cross-sections so as to enable analysis of the abnormal waveform for determining timing and amplitude on the time axis with reference to the back scale.

Thus, in the conventional system, it is necessary to form a hard copy of the freeze waveform in the event that any abnormality is recognized during observation. Thus, the work for finding any abnormality in the waveform is quite laborious and detailed analysis of the waveform cannot be conducted when no recorder is available.

SUMMARY OF THE INVENTION

Accordingly, an object of the present invention is to provide an apparatus for displaying waveform of a physiological signal, which enables detailed observation of the waveform without requiring any recorder.

To this end, according to the present invention, there is provided an apparatus for displaying waveform of a physiological signal which can continuously display waveform of the physiological signal and which can freeze the waveform as required, wherein, when the physiological signal waveform is displayed continuously, the back scale is not displayed or the brightness display of the back scale is lowered, whereas, when the physiological signal waveform is displayed as a freeze image, the brightness of the display of the back scale is increased.

According to the present invention, when a physiological signal such as a cardiographic signal is displayed in a still state on a monitor screen, a back scale is simultaneously displayed at a high brightness to enable detailed analysis, thus eliminating necessity for the production of hard copy by, for example, a recorder which is necessitated in the conventional monitoring system. It is therefore possible to observe and examine the abnormal waveform by making reference to the back scale displayed on the monitor screen.

As a consequence, the present invention offers advantages in that a quick diagnosis of the physiological signal waveform is made possible and in that observation of a freeze image is possible even when no recorder is available.

In addition, observation of continuous waveform can De conducted without being hindered by the back scale because the display of the back scale is not conducted or made at a reduced brightness during displaying the continuous waveform.

The above and other objects, features and advantages of the present invention will become clear from the following description of the preferred embodiment when the same is read in conjunction with the accompanying drawings.

DESCRIPTION OF THE PREFERRED EMBODIMENT

Figure 1:
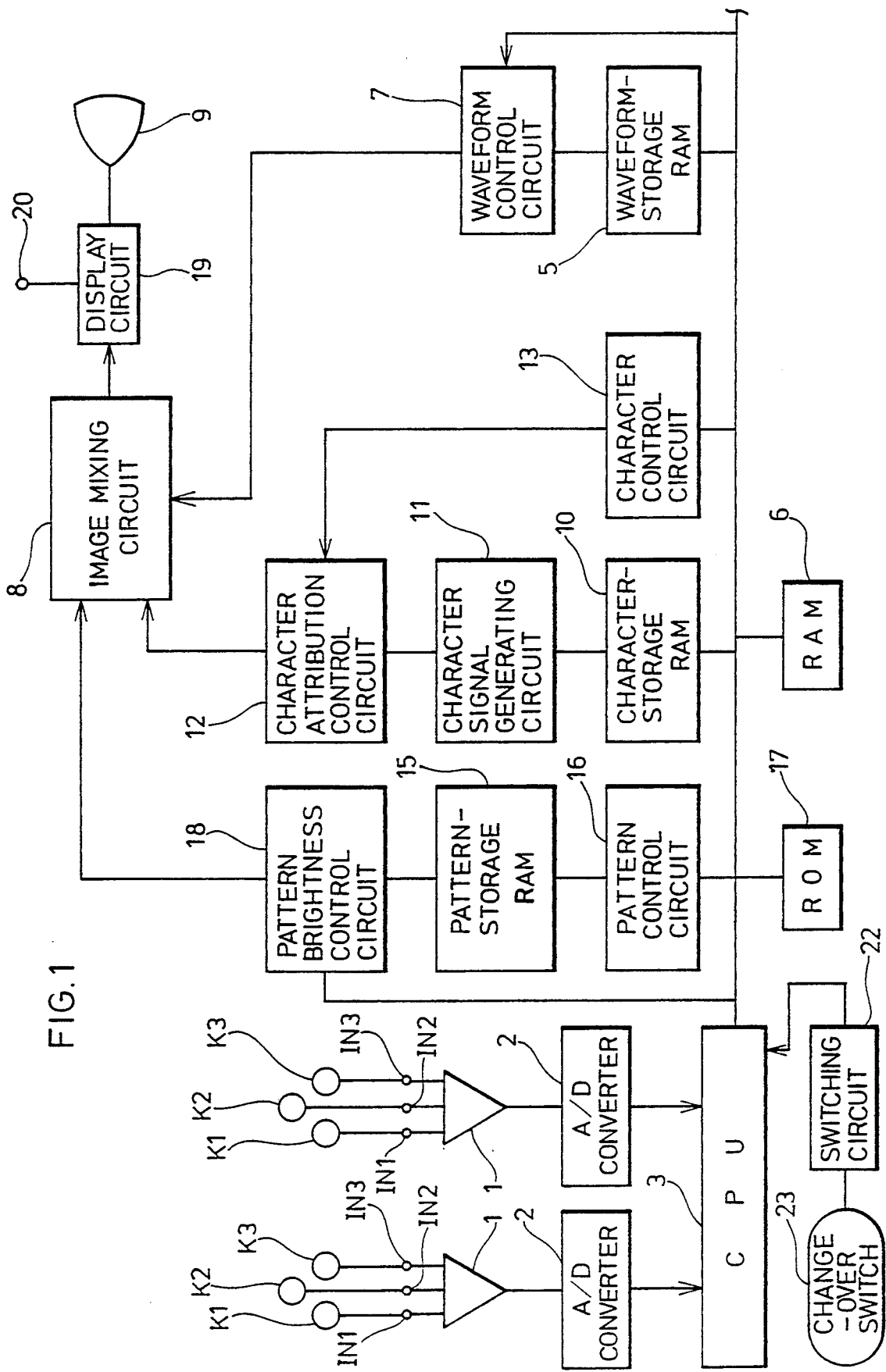
FIG. 1 is a block diagram of an embodiment of the apparatus of the present invention for displaying waveform of a physiological signal.

FIG. 1 is a block diagram of an embodiment of the apparatus of the present invention for displaying waveform of a physiological signal. This embodiment, applied to a cardiographic apparatus, can simultaneously display cardiograms of a plurality of patients, e.g., 8 patients. This display apparatus, when it is used in a mode for displaying continuous waveform, does not display the back scale composed of cross-sections or displays the back scale with a reduced level of brightness, unlike the known display apparatus which displays such a back scale together with the continuous signal waveform. The apparatus, however, displays the back scale with enhanced brightness when it is used in a mode for displaying still or freeze waveform, so that the user can examine the freeze waveform by making reference to the back scale.

Referring to FIG. 1, signals picked up by cardiographic measuring electrodes K1, K2, K3 on the patient bodies are input to input terminals IN1, IN2, IN3 of the respective amplifiers and the amplified cardiographic signals output from the amplifiers are A/D converted by analog-to-digital converters 2 the digital outputs of which are delivered to a central processing unit (CPU) 3.

The cardiographic signals delivered the CPU 3 are stored in random access memories (RAMs) 5 and 6 through a system BUS 4 composed of a data BUS and an address BUS. The cardiographic signal stored in the RAM 6 is delivered to a recorder (not shown) which is connected to the system BUS4 through an input/output (I/O) interface (not shown) or output to the exterior of the system through a communication interface such as RS232C. The cardiographic signal stored in the RAM for storing waveform is read out in real time .and delivered to a waveform control circuit 7. The waveform control circuit 7 conducts a waveform amplitude control for the purpose of displaying the cardiogram at a predetermined sensitivity in accordance with instructions given by the CPU 3. The cardiographic signal after the amplitude control is delivered to an image mixer circuit 8. A later-mentioned monitor 9 displays the freeze image unless the writing of cardiographic signal in the waveform-storage RAM 5 is conducted.

A character-storage RAM 10, which is connected to the CPU 3 through the system BUS 4, stores character data such as the bed ID No., heart rate computed by the CPU, ST value and so forth. Data read from the character storage RAM ! 0 is converted into character signals by character signal generating circuit 11 and the character signals thus formed are supplied to character attribution control circuit 12. The character attribution control circuit 12 conducts attribution controls such as reverse of display on the input character signals, in accordance with control signal delivered by a character control circuit 13. The character signal after the attribution control is delivered to the image mixer circuit 8. In the example of the display shown in FIG. 3, the character denoted by numeral 14 is the reverse display.

A pattern-storage RAM 15, upon receipt of a control signal from a pattern control circuit 16 connected to the CPU 3 through the system BUS 4, provides pattern data to a pattern brightness control circuit. Pattern data for the back scale which is beforehand stored in a ROM 17 which also stores operation programs for the CPU and other data. The back scale is formed by a cross-section composed of axis of ordinate representing the time axis scale and an abscissa which shows the amplitude scale.

The back scale pattern data read from the RAM 15 is supplied to a pattern brightness control circuit 18 which operates under the control of the CPU 3. The pattern brightness control circuit 18 conducts a control of the brightness of the back scale in accordance with the form of display of cardiograph on the basis of the control signal from the CPU 3. More specifically, the control is conducted such as to lower the brightness of the back scale when the cardiogram is displayed in the form of a continuous waveform and to increase the brightness of the back scale when the cardiogram is displayed in the form of a freeze waveform. The back scale signal after the brightness control, output from the pattern brightness control circuit 18, is supplied to the image mixer circuit 8. The image mixer circuit 8 synthesizes a synthetic output from the cardiographic signal, character signal and the back scale signal. The synthetic output is then displayed on a display circuit 19.

The display circuit 19 forms a monitor display signal which can be input to a display monitor 9 which may be a CRT. It is possible to control the brightness of the whole display image by inputting a brightness control signal to the input terminal 20 which is connected to the display circuit 19. The display monitor 9 may be constituted by means other than a CRT, e.g., a liquid crystal display device.

Figure 3:
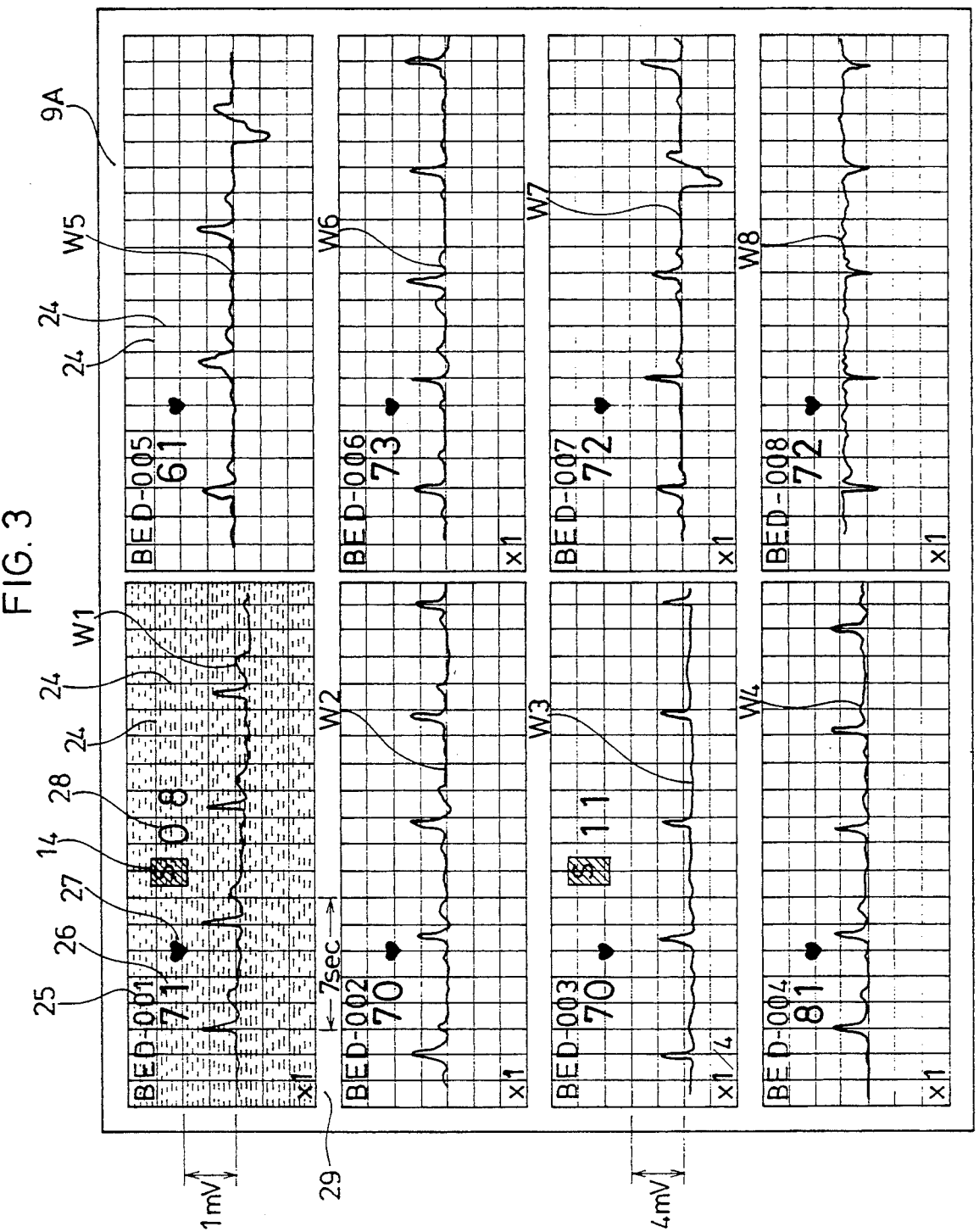
FIG. 3 is an illustration of an example of a freeze waveform displayed on the monitoring screen of the apparatus shown in FIG. 1.

As a consequence, cardiograms W1 to W8, character 26 and the back scales 24 are simultaneously displayed on the screen 9A of the display monitor 9 as shown in FIG. 3, as the monitor display signal is supplied from the display circuit 19 to the display monitor 9.

A change-over switch 23 connected to the CPU 3 through a switching circuit 22 is adapted for performing switching between the mode for displaying the continuous waveform and the mode for displaying the freeze image. The user pushes this switch when he has recognized any abnormal waveform during observation of continuous cardiographic signal displayed on the display screen 9A, so that the user can observe a still image, i.e., freeze waveform, of a portion of the continuous cardiographic signal waveform.

The waveform-storage RAM 5, the waveform control circuit 7 and the CPU 3 form a waveform display control means, while the pattern control circuit 16, pattern-storage RAM 15, pattern brightness control circuit 13 and the CPU in cooperation form a pattern display control means. The image mixer circuit 8 and the display circuit 19 in cooperation form display processing means.

Figure 2:
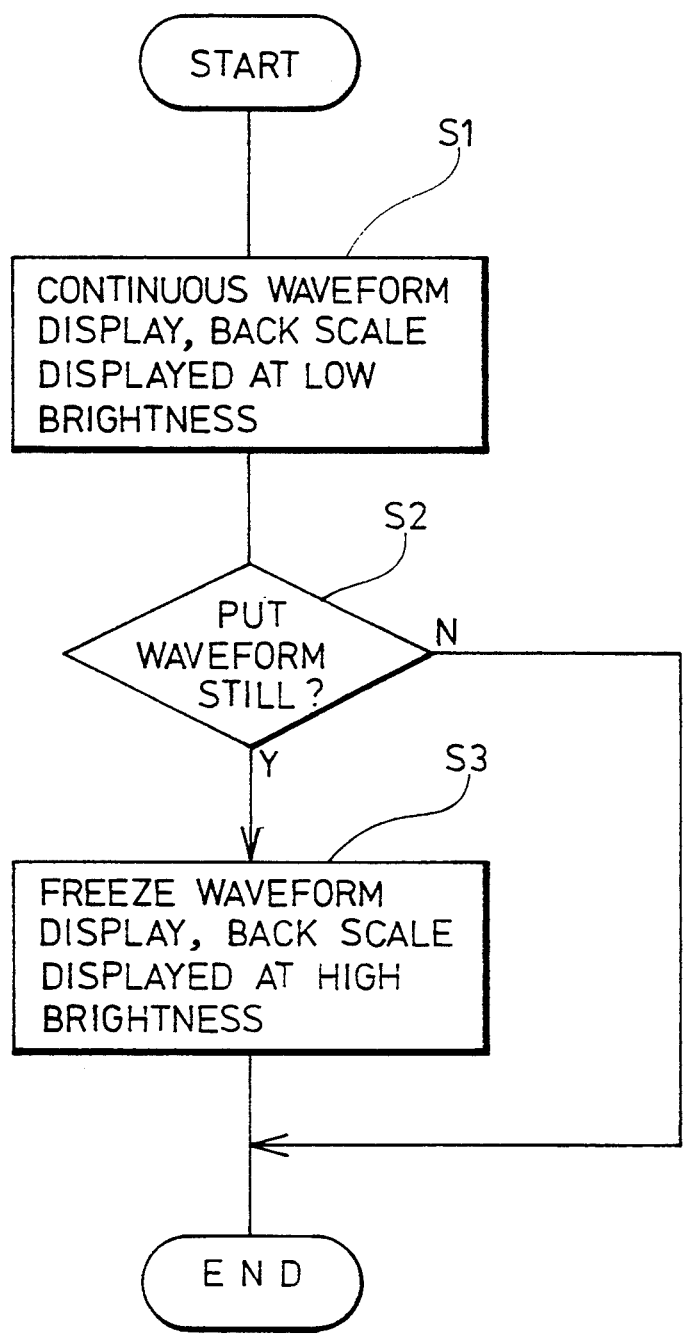
FIG. 2 is a flowchart illustrative of the operation of the apparatus shown in FIG. 1.

FIG. 2 shows the flow of a process of operation of the physiological signal waveform display apparatus having the described construction. As the operation is started, continuous cardiographic signal waveform is displayed on the monitor screen 9A as shown in FIG. 3. At the same time, the back scales 24 is displayed at a low brightness together with the cardiographic signal. (Step S1)

In Step S2, the change-over switch 23 is pushed so that the cardiograph is displayed as a freeze waveform on the display screen 9A. In this case, the back scales 24 are displayed at high level of brightness together with the cardiogram.(Step S3)

FIG. 3 shows an example of the display of the freeze waveform of a cardiogram on the monitor screen 9A. It will be seen that cardiographic freeze waveforms W1 to W8, corresponding to the bed ID Nos. representing individual patients,are displayed together with the back scales 24. In FIG. 3, minute gradations of the back scales are omitted for the cardiograms W2 to W8 for the purpose of clarification of the drawings. The cardiographic waveforms are displayed at the highest brightness, while characters representing data such as the bed ID No. 25, heart rates 26, heart marks 27 representing rhythm, the ST value 28 and the waveform sensitivity levels 29 are displayed at medium level brightness. The back scales 24 are displayed at the lowest brightness. It is thus possible to obtain a display image which is substantially equivalent to that of a hard copy produced by a recorder. The moving velocity of the cardiographic signal waveform in the direction of ordinate is 25 mm/sec which is common to all cardiograms. The moving velocity in the direction of abscissa is 1 mV/cm in the case of the cardiogram W1 and 4 mV/cm in the case of the cardiogram W3.

In the described embodiment, the display of the back scales is not suspended but is conducted at the low brightness during display of the cardiographic signal waveform in the continuous display mode. This, however, is only illustrative and the arrangement may be such that the brightness of display of the back scales is reduced to zero, i.e., the display of the back scales is completely omitted, during the display of the continuous cardiographic signal waveform. The invention also can be carried out so as to display only one cardiogram at one time, although the described embodiment is constructed to simultaneously display a plurality of cardiograms.

It is also to be understood that the present invention can equally be applied to display of other types of physiological signal waveforms such as blood pressure signals waveform, EEG, EMG and so forth, although a cardiographic display has been specifically described.

What is claimed is:

1. An apparatus for displaying a waveform of a physiological signal, comprising:

waveform display control means for picking up said physiological signal and for conducting a control for displaying the waveform of said physiological signal;

switching means having a first mode of operation and a second mode of operation for displaying the waveform of said physiological signal as one of a continuous waveform and a freeze waveform, wherein said waveform is displayed as a continuous waveform in said first mode and said waveform is displayed as a freeze waveform in said second mode;

pattern display control means for forming a pattern signal of a back scale which is displayed simultaneously with the waveform of said physiological signal and for conducting a control to vary the brightness of the display of said backscale to increase said back scale brightness when said switching means is in said second mode to facilitate instantaneous evaluation of the freeze waveform and decrease said back scale brightness so as not to hinder observation of said continuous waveform when said switching means is in said first mode;

display processing means for synthesizing a monitor display signal from said physiological signal output from said waveform display control means and said pattern signal of said backscale; and display monitor means for receiving said monitor display signal from said display processing means so as to simultaneously display one of the continuous and freeze waveforms of said physiological signal and said backscale on a display screen thereof thereby enabling instantaneous evaluation of said continuous and freeze waveforms without a recorder.

2. An apparatus for displaying a waveform of a physiological signal according to claim 1, wherein said waveform display control means includes a waveform-storage RAM which successively stores said physiological signal while allowing the stored physiological signal to be successively read therefrom when said switching means is in said first mode displaying said continuous waveform of said physiological signal, said RAM, allows the same physiological signal waveform stored therein to be read repeatedly as a freeze waveform when said switching means is in said second mode.

3. An apparatus for displaying a waveform of a physiological signal according to claim 1, wherein said pattern display control means includes a RAM for storing pattern data of the back scale to be displayed, and a pattern brightness control circuit for varying the brightness of the back scale.

4. An apparatus for displaying a waveform of a physiological signal according to claim 1, wherein said pattern display control means operates to materially inhibit the display of said back scale when said switching means is in said first mode of operation displaying said continuous waveform.

5. An apparatus for displaying a waveform of a physiological signal according to claim 1, wherein said switching means is a manually operable switch.

6. An apparatus for displaying a waveform of a physiological signal according to claim 1, further comprising character attribution control means coupled to said waveform display control means for receiving character data from said physiological signal and providing a character signal to said monitor display signal for displaying said character data.

7. An apparatus for displaying a waveform of a physiological signal according to claim 1, further comprising an image display intensity control means coupled to said display monitor means for varying the brightness intensity of the waveform displayed.

8. An apparatus for displaying a waveform of a physiological signal according to claim 1, wherein said back scale comprises a horizontal axis and a vertical axis forming a grid.

* * * * *